United States Patent [19]

Zeidler et al.

[11] 4,236,022
[45] Nov. 25, 1980

[54] ESTERS OF 1,2-DIHYDROXYALKANES AS COSMETIC EMULSIFIERS AND COSMETIC EMULSIONS CONTAINING THEM

[75] Inventors: Ulrich Zeidler; Fanny Scheuermann, both of Düsseldorf, Fed. Rep. of Germany

[73] Assignee: Henkel Kommanditgesellschaft auf Aktien (Henkel KGaA), Düsseldorf-Holthausen, Fed. Rep. of Germany

[21] Appl. No.: 972,014

[22] Filed: Dec. 21, 1978

[30] Foreign Application Priority Data

Dec. 22, 1977 [DE] Fed. Rep. of Germany ....... 2757278

[51] Int. Cl.³ ...................... C07C 69/38; C07C 69/40; C07C 69/70; C07C 69/675
[52] U.S. Cl. ...................................... 560/198; 560/55; 560/60; 560/76; 560/112; 560/181; 560/182; 560/186; 560/187; 560/200; 560/89; 560/189; 560/227; 560/230
[58] Field of Search .................. 560/182, 198, 200, 55, 560/60, 76, 112, 181, 186, 187, 89, 189, 227, 230

[56] References Cited

U.S. PATENT DOCUMENTS

| | | | |
|---|---|---|---|
| 2,821,542 | 1/1958 | Schmutzler | 560/34 |
| 3,746,744 | 7/1973 | Reid, Jr. | 560/182 |
| 3,933,923 | 1/1976 | Osberghaus | 568/866 |
| 3,951,945 | 4/1976 | Heesen et al. | 536/4 |
| 3,968,135 | 7/1976 | Steele et al. | 560/200 |

*Primary Examiner*—Natalie Trousof
*Assistant Examiner*—L. Hendriksen

*Attorney, Agent, or Firm*—Hammond & Littell, Weissenberger and Muserlian

[57] ABSTRACT

Mono- and dicarboxylic acid esters of 1,2-dihydroxyalkanes of the formulae

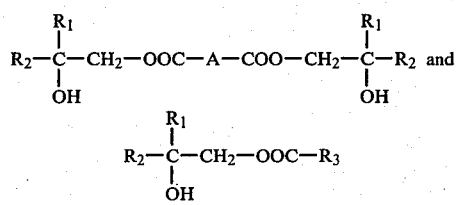

wherein A represents a bivalent radical selected from the group consisting of alkylene having from 1 to 16 carbon atoms, hydroxyalkylene having from 1 to 8 carbon atoms and 1 to 4 hydroxys, alkenylene having from 2 to 18 carbon atoms, alkoxyalkylene having from 2 to 6 carbon atoms, phenylene, alkylphenylene having from 1 to 12 carbon atoms in the alkyl; $R_1$ represents a member selected from the group consisting of hydrogen and alkyl having from 1 to 12 carbon atoms; $R_2$ is alkyl having from 10 to 22 carbon atoms; and $R_3$ represents a member selected from the group consisting of hydroxyalkyl having from 1 to 4 carbon atoms, phenylhydroxyalkyl having from 1 to 4 carbon atoms in the alkyl and haloalkyl having from 1 to 4 carbon atoms; as well as water-in-oil emulsions containing from 1% to 20% by weight of said esters, from 20% to 75% by weight of water and the remainder to 100% by weight conventional oily substances used in cosmetic emulsions.

7 Claims, No Drawings

ESTERS OF 1,2-DIHYDROXYALKANES AS COSMETIC EMULSIFIERS AND COSMETIC EMULSIONS CONTAINING THEM

BACKGROUND OF THE INVENTION

Simple monocarboxylic acid esters of vicinal alkanediols are known compounds useful as foam-inhibitors in washing compositions, as described in U.S. Pat. No. 3,993,605. This patent however describes fatty acid and benzoic acid mono and diesters of non-terminal vicinal alkanediols having 12 to 32 carbon atoms.

Copending, commonly assigned U.S. Patent application Ser. No. 837,691 also describes fatty acid and benzoic acid monesters of terminal and non-terminal vicinal alkanediols having from 8 to 20 carbon atoms, which are alkoxylated to give low-foaming surface-active compounds useful as clear-rinse agents in mechanical dishwashers.

In contrast to the production of oil-in-water emulsions, only a limited number of emulsifying agents are available for producing cosmetic emulsions of the water-in-oil type and, moreover, the best of these emulsifying agents are becoming increasingly scarce. Even nowadays, wool fat and its derivatives are still some of the most important bases for emulsifying agents for producing creams of the water-in-oil type. However, despite their uncontested advantages, wool fat and its derivatives, such as lanolin, have certain disadvantages. Thus, conventional water-in-oil emulsifying agents based on wool fat and its derivatives impart a strong characteristic odor to the creams prepared with these substances. This in turn, requires strong perfuming which frequently cannot be tolerated by persons having sensitive skin. However, this influencing of the quality of the cream by a strong characteristic odor is not only peculiar to wool fat and its derivatives, but also extends to lanolin-free water-in-oil emulsifying agents based on animal sterols, particularly such emulsifying agents based on cholesterol. Furthermore, low-molecular weight emulsifying agents, together with the effective substances of the cream, can be absorbed by the skin, which is not desirable in all cases.

In addition to the said emulsifying agents based on wool fat, wax alcohols and sterols, the most widely known water-in-oil emulsifiers for cosmetic purposes include the oleic acid esters of various polyols, such as glycerine, pentaerythritol, trimethylolpropane and sorbitol. However, due to the unsaturated character in their acid component, the oleic acid esters have various disadvantages with respect to their technical use, so that there is a genuine need for new and suitable water-in-oil emulsifying agents.

OBJECTS OF THE INVENTION

An object of the present invention is the development of mono and dicarboxylic acid esters of 1,2-dihydroxyalkanes having from 12 to 32 carbon atoms which are useful as emulsifiers for water-in-oil emulsions.

Another object of the present invention is the development of mono- and dicarboxylic acid esters of 1,2-dihydroxyalkanes of the formulae

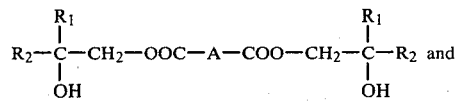

-continued

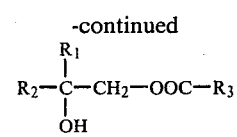

wherein A represents a bivalent radical selected from the group consisting of alkylene having from 1 to 16 carbon atoms, hydroxyalkylene having from 1 to 8 carbon atoms and 1 to 4 hydroxys, alkenylene having from 2 to 18 carbon atoms, alkoxyalkylene having from 2 to 6 carbon atoms, phenylene, alkylphenylene having from 1 to 12 carbon atoms in the alkyl; $R_1$ represents a member selected from the group consisting of hydrogen and alkyl having from 1 to 12 carbon atoms; $R_2$ is alkyl having from 10 to 22 carbon atoms; and $R_3$ represents a member selected from the group consisting of hydroxyalkyl having from 1 to 4 carbon atoms, phenylhydroxyalkyl having from 1 to 4 carbon atoms in the alkyl and haloalkyl having from 1 to 4 carbon atoms.

As further object of the present invention is the development of a cosmetic emulsion or cream of the water-in-oil type which can be prepared easily and safely from inexpensive materials without need for costly emulsifying equipment.

A yet further object of the present invention is the development of a cosmetic emulsion of the above type which is substantially odorless and which, therefore, can find general acceptance when containing only a small and harmless amount of perfume.

A still further object of the present invention is the production of a cosmetic emulsion of the above type comprising (1) from 1% to 20% by weight of an ester emulsifier capable of forming water-in-oil emulsions, said ester emulsifier being at least one mono or dicarboxylic acid ester of 1,2-dihydroxyalkane of the above formula, (2) from 20 to 75% by weight of water; and (3) the remainder to 100% by weight of conventional oil substances used in cosmetic emulsions.

These and other objects of the present invention will become more apparent as the description thereof proceeds.

DESCRIPTION OF THE INVENTION

This invention relates generally to mono- and dicarboxylic acid-2-hydroxy-alkyl esters of the following general formula

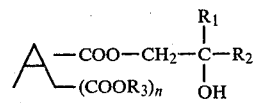

in which A represents an alkyl(ene), a cycloalkyl(ene) or an aryl(ene) group which may be substituted or interrupted by hetero atoms; $R_1$ represents hydrogen or an alkyl group with from 1 to 12 carbon atoms; $R_2$ represents an alkyl group with from 10 to 22 carbon atoms; $R_3$ represents hydrogen or a group

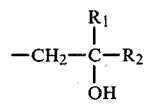

and n has the value 0 or 1.

More particularly, the present invention relates to mono- and dicarboxylic acid esters of 1,2-dihydroxyalkanes of the formulae

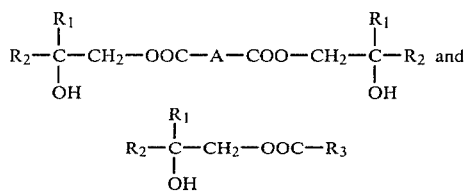

wherein A represents a bivalent radical selected from the group consisting of alkylene having from 1 to 16 carbon atoms, hydroxyalkylene having from 1 to 8 carbon atoms and 1 to 4 hydroxys, alkenylene having from 2 to 18 carbon atoms, alkoxyalkylene having from 2 to 6 carbon atoms, phenylene, alkylphenylene having from 1 to 12 carbon atoms in the alkyl; $R_1$ represents a member selected from the group consisting of hydrogen and alkyl having from 1 to 12 carbon atoms; $R_2$ is alkyl having from 10 to 22 carbon atoms; and $R_3$ represents a member selected from the group consisting of hydroxyalkyl having from 1 to 4 carbon atoms, phenylhydroxyalkyl having from 1 to 4 carbon atoms in the alkyl and haloalkyl having from 1 to 4 carbon atoms.

The invention also relates to water-in-oil emulsions containing (1) from 1% to 20% by weight of an ester emulsifier capable of forming water-in-oil emulsions, said ester emulsifier being at least one mono or dicarboxylic acid ester of 1,2-dihydroxyalkane of the above formula, (2) from 20 to 75% by weight of water; and (3) the remainder to 100% by weight of conventional oil substances used in cosmetic emulsions.

The mono- and dicarboxylic acid-2-hydroxy-alkyl esters according to the invention may be prepared by the known method of reacting mono- or dicarboxylic acids of the following general formula

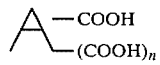

or the formulae HOOC—A—COOH and HOOC—$R_3$ with epoxides of the following general formula

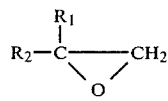

wherein $\bigwedge$ A, $R_1$, $R_2$ and $R_3$ and n have the meanings specified above, preferably in the presence of a weakly alkaline catalyst, such as a quaternary ammonium compound.

An alternative method of preparing the mono- and dicarboxylic acid-2-hydroxy-alkyl esters according to the invention consists of esterifying mono- and dicarboxylic acids of the following general formula

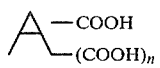

or the formulae HOOC—A—COOH and HOOC—$R_3$ with alkanediols of the following general formula

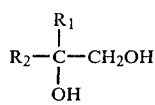

wherein $\bigwedge$, A, $R_1$, $R_2$, $R_3$ and n have the meanings given above, by commonly known methods of esterification.

Suitable-dicarboxylic acid components are chiefly those in which the carboxyl groups are close together (that is not separated by more than a chain of 4 methylene groups), such as malonic acid, succinic acid, glutaric acid, adipic acid, maleic acid, fumaric acid, malic acid, tartaric acid, tartronic acid, itaconic acid and citraconic acid. In particular, the above acids are alkanedioic acids, having from 3 to 18 carbon atoms, hydroxyalkanedioic acids having from 3 to 10 carbon atoms and 1 to 4 hydroxys, alkanedioic acids having from 4 to 20 carbon atoms, carboxyalkoxyalkanoic acids having from 4 to 8 carbon atoms, benzene dicarboxylic acids, and alkylbenzene dicarboxylic acids having from 1 to 12 carbon atoms in the alkyl.

In the case of monocarboxylic acids, it is found advantageous to use short chain compounds substituted with hydroxyl, halogen or ether groups, such as glycolic acid, lactic acid, chloracetic acid or mandelic acid. In particular, the above monocarboxylic acids are hydroxyalkanoic acids having from 2 to 5 carbon atoms, phenylhydroxyalkanoic acids having from 2 to 5 carbon atoms in the alkanoic chain, and haloalkanoic acids having from 2 to 5 carbon atoms.

The dicarboxylic acids esters are particularly important as carboxylic acid components useful as water-in-oil emulsifiers.

The vicinal alkane epoxides and vicinal alkane diols as the other starting components for the carboxylic acid-2-hydroxy-alkyl esters according to the invention are obtained in known manner from the corresponding olefins or olefin mixtures. Mixtures of epoxides or diols of varying chain lengths would generally be used, for example $C_{12-18}$, $C_{16-18}$, $C_{16-20}$ and $C_{16-24}$-alkane-1,2-epoxides or alkane-1,2-diols.

It is also possible to use olefin mixtures which are prepared by aluminochemical methods and which have unbranched alkyl chains with 12 to 20 carbon atoms. These mixtures have a high (i.e., more than 50%) proportion of terminal unsaturation. Examples of suitable commercial products are those having the chain length distributions shown below:

| Olefin Fractions Used | |
|---|---|
| Fraction | % by Weight |
| (a) $C_{12}$-$C_{14}$ - fraction | |
| $C_{12}$ Terminal | 55 |
| $C_{14}$ Terminal | 31 |
| $C_{12}$ Non-Terminal | 5 |
| $C_{14}$ Non-Terminal | 8 |
| (b) $C_{14}$-$C_{16}$ - fraction | |
| $C_{14}$ Terminal | 53 |
| $C_{16}$ Terminal | 28 |
| $C_{14}$ Non-Terminal | 7 |
| $C_{16}$ Non-Terminal | 11 |
| (c) $C_{16}$-$C_{18}$ - fraction | |
| $C_{16}$ Terminal | 35 |
| $C_{18}$ Terminal | 23 |
| $C_{20}$ Terminal | 2 |
| $C_{16}$ Non-Terminal | 11 |
| $C_{18}$ Non-Terminal | 21 |

| Olefin Fractions Used | |
|---|---|
| Fraction | % by Weight |
| $C_{20}$ Non-Terminal | 5 |

The mono- and dicarboxylic acid-2-hydroxy-alkyl esters according to the invention therefore include the following, given as examples: Lactic acid-2-hydroxy-$C_{12/14}$-alkyl ester, -$C_{16/18}$-alkyl ester and -$C_{18/20}$-alkyl ester; chloroacetic-2-hydroxy-$C_{16/18}$-alkyl ester; malonic acid-di-2-hydroxy-$C_{12/14}$-alkyl ester and -$C_{16/18}$-alkyl ester; succinic acid-di-2-hydroxy-$C_{12/14}$-alkyl ester, -$C_{16/18}$-alkyl ester and -$C_{18/20}$-alkyl ester; glutaric acid-di-2-hydroxy-$C_{12/14}$-alkyl ester and -$C_{16/18}$-alkyl ester; maleic acid-di-2-hydroxy-$C_{12/14}$-alkyl ester, -$C_{16/18}$-alkyl ester and -$C_{18/20}$-alkyl ester; fumaric acid-di-2-hydroxy-$C_{12/14}$-alkyl ester and -$C_{16/18}$-alkyl ester; malic acid-di-2-hydroxy-$C_{12/14}$-alkyl ester and -$C_{16/18}$-alkyl ester; tartaric acid-di-2-hydroxy-$C_{12/14}$-alkyl ester and -$C_{18/20}$-alkyl ester; adipic acid-di-2-hydroxy-$C_{12/14}$-alkyl ester and $C_{16/18}$-alkyl ester; tartronic acid-di-2-hydroxy-$C_{16/18}$-alkyl ester; citraconic acid-di-2-hydroxy-$C_{16/18}$-alkyl ester; itaconic acid-di-2-hydroxy-$C_{16/18}$-alkyl ester; diglycolic acid-di-2-hydroxy-$C_{16/18}$-alkyl ester; mucic acid-di-2-hydroxy-$C_{16/18}$-alkyl ester; phthalic acid-di-2-hydroxy-$C_{16/18}$-alkyl ester; hexadecenylsuccinic acid-di-2-hydroxy-$C_{16/18}$-alkyl ester and mandelic acid-2-hydroxy-$C_{16/18}$-alkyl ester.

The mono- and dicarboxylic acid-2-hydroxy-alkyl esters according to the invention are very suitable for use as water-in-oil emulsifiers, particularly for the preparation of cosmetic emulsions of the water-in-oil type. Special advantages of these emulsifiers include their spontaneous emulsifying action and the smooth and glossy appearance of creams prepared with them. The ease with which creams prepared from them can spread over the skin should also be particularly mentioned. The creams are not sticky and leave an agreeable feeling on the skin. The emulsifiers are colorless and odorless and not liable to oxidize. Emulsions prepared from them are generally well tolerated by persons with a sensitive skin. Since they have no substantial odor, they do not need to be strongly perfumed, which makes them better tolerated by the skin as well as saving cost.

Among the mono- and dicarboxylic acid-2-hydroxy-alkyl esters according to the invention, particularly important for their emulsifier properties are those products which are derived from dicarboxylic acids, and among these, especially those derived from dicarboxylic acids in which the alkylene group has from 1 to 4 carbon atoms. In view of the alcoholic ester component, the optimum effect is obtained with an average chain length of from 12 to 20 carbon atoms. The preferred dicarboxylic acid-2-hydroxy-alkyl esters are therefore compounds corresponding to the following general formula:

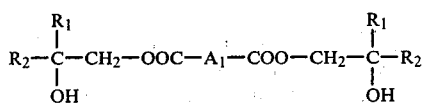

wherein $A_1$ is a number selected from the group consisting of alkylene having from 1 to 4 carbon atoms and alkenylene having from 2 to 4 carbon atoms, $R_1$ is hydrogen and $R_2$ is alkyl having from 10 to 18 carbon atoms.

The emulsions according to the invention are prepared by the simple and well-known method of dissolving the mono- and dicarboxylic acid-2-hydroxyalkyl esters, acting as emulsifiers, in the oily phase at elevated temperatures in the region of 60° to 70° C. and then adding the desired quantity of water preheated to about 60° to 65° C. The resulting emulsion is stirred until cold.

Cosmetically effective amounts of further constituents of the cosmetic emulsions being manufactured, such as skin moisture regulators, vegetable extracts of effective substances, vitamins, hormones, pigments, salts, perfume oils, UV filtering substances, dyestuffs, etc., are advantageously dissolved or distributed in the phase which absorbs these substances to best advantage. The quantity of emulsifying agent required is 1% to 20% by weight, preferably 2% to 10% by weight, relative to the total cosmetic emulsion. The amount of water to be incorporated can be 20% to 75% by weight, preferably 45% to 65% by weight, relative to the total cosmetic emulsion.

Products conventionally used, such as animal and vegetable oils and fats, synthetic esters of fatty acids with aliphatic alcohols, higher fatty alcohols, waxes, so-called mineral fats and oils, such as paraffin oil, "Vaseline" ®, ceresine, silicone oils and silicone fats are suitable as the oily phase of the cosmetic emulsions in accordance with the invention.

The invention thus also includes a composition which when agitated with water forms a cosmetic emulsion of the water-in-oil type, comprising (1) from 1% to 20% by weight, relative to the total weight of said composition, of the mono- and dicarboxylic acid-2-hydroxyalkyl esters according to the invention, and (2) the remainder to 100% by weight of the composition of conventional oily substances used in cosmetic emulsions. Such conventional oily substances include vegetable and animal oils and fats, synthetic esters of fatty acids with aliphatic alcohols, higher fatty alcohols, waxes, so-called mineral fats and oils, such as paraffin oil, "Vaseline" ®, ceresin, silicone oils and silicone fats. In addition to the cosmetic emulsions or creams can contain, if desired, other auxiliary substances normally used in cosmetic emulsions. Examples of such auxiliary substances are skin moisture regulators, vegetable extracts of effective substances, vitamins, hormones, pigments, salts, perfume oils, UV filtering substances, dyestuffs, etc.

The following Examples are intended to further explain the invention, but without limiting the invention to these Examples.

EXAMPLES

The preparation of several mono- and dicarboxylic acid-2-hydroxy-alkyl esters according to the invention will first be described.

(A) Malonic acid-di-2-hydroxy-$C_{16/18}$-alkyl esters 104 gm of malonic acid (1 mol) were heated to 120° C. with 254 gm of $C_{16/18}$-alkane-1,2-epoxide (2 mol) in the presence of 2% by weight (7 gm) of benzyl-dimethyl-alkyl ammonium chloride for 4½ hours with stirring. A colorless product with a soft, unctuous texture was obtained on cooling. The product had the following characteristic values: OH number: 146; saponification number: 125; acid number: 1.

The other mono- and dicarboxylic acid-2-hydroxy-alkyl esters were obtained similarly from dicarboxylic acid and epoxide in a molar ratio of 1:2 or mono-carboxylic acid and epoxide in a molar ratio of 1:1. The products obtained are colorless ointment-like substances varying from soft to firm; their characteristic values are given in the following Table.

| Chemical Name | OH Number | Saponification Number | Acid Number |
|---|---|---|---|
| B Succinic acid-di-2-hydroxy-$C_{16/18}$-alkyl ester | 138 | 172 | 10 |
| C Glutaric acid-di-2-hydroxy-$C_{16/18}$-alkyl ester | 135 | 168 | 12 |
| D Adipic acid-di-2-hydroxy-$C_{16/18}$-alkyl ester | 134 | 168 | 12 |
| E Tartronic acid-di-2-hydroxy-$C_{16/18}$-alkyl ester | 222 | 113 | 3 |
| F Maleic acid-di-2-hydroxy-$C_{16/18}$-alkyl ester | 136 | 172 | 18 |
| G Fumaric acid-di-2-hydroxy-$C_{16/18}$-alkyl ester | 148 | 166 | 8 |
| H Citraconic acid-di-2-hydroxy-$C_{16/18}$-alkyl ester | 143 | 155 | 9 |
| J Itaconic acid-di-2-hydroxy-$C_{16/18}$-alkyl ester | 140 | 160 | 7 |
| K Hexadecenylsuccinic acid-di-2-hydroxy-$C_{16/18}$-alkyl ester | 97 | 123 | 2 |
| L Malic acid-di-2-hydroxy-$C_{16/18}$-alkyl ester | 164 | 170 | 36 |
| M Tartaric acid-di-2-hydroxy-$C_{16/18}$-alkyl ester | 220 | 163 | 20 |
| N Diglycollic acid-di-2-hydroxy-$C_{16/18}$-alkyl ester | 127 | 167 | 17 |
| O Mucic acid-di-2-hydroxy-$C_{16/18}$-alkyl ester | 210 | 130 | 20 |
| P Phthalic acid-di-2-hydroxy-$C_{16/18}$-alkyl ester | 131 | 158 | 12 |
| Q Malonic acid-di-2-hydroxy-$C_{12/14}$-alkyl ester | 201 | 166 | 1 |
| R Succinic acid-di-2-hydroxy-$C_{12/14}$-alkyl ester | 195 | 208 | 9 |
| S Glutaric acid-di-2-hydroxy-$C_{12/14}$-alkyl ester | 190 | 202 | 8 |
| T Maleic acid-di-2-hydroxy-$C_{12/14}$-alkyl ester | 178 | 206 | 18 |
| U Fumaric acid-di-2-hydroxy-$C_{12/14}$-alkyl ester | 198 | 209 | 7 |
| V Malic acid-di-2-hydroxy-$C_{12/14}$-alkyl ester | 238 | 202 | 27 |
| W Tartaric acid-di-2-hydroxy-$C_{12/14}$-alkyl ester | 310 | 195 | 23 |
| X Succinic acid-di-2-hydroxy-$C_{18/20}$-alkyl ester | 141 | 154 | 4 |
| Y Lactic acid-2-hydroxy-$C_{16/18}$-alkyl ester | 272 | 147 | 34 |
| Z Chloroacetic acid-2-hydroxy-$C_{16/18}$-alkyl ester | 90 | 291 | 32 |
| A' Mandelic acid-2-hydroxy-$C_{16/18}$-alkyl ester | 139 | 219 | 17 |

The cosmetic water-in-oil skin creams mentioned below were prepared using the mono- and dicarboxylic acid-2-hydroxy-alkyl esters mentioned above as emulsifiers.

To prepare the creams the emulsifier was dissolved in the oily components and the resulting oil phase was heated to 60° C. Salts, preservatives and other water-soluble constituents were dissolved in the required quantity of water and the resulting aqueous phase was heated to 65° C. The aqueous phase was then introduced slowly into the oil phase with stirring and the whole mass continued to be stirred until cold. Stable, smooth, glossy creams were obtained in all cases. Skin creams for various purposes can be prepared from this basic cream by the incorporation of other active ingredients such as skin moisture regulators, plant extracts, perfume oils, etc.

EXAMPLE 1

Cream based on hardened peanut oil/decyl oleate mixture

| | Parts by Weight |
|---|---|
| Hardened peanut oil | 20 |
| Decyl oleate | 20 |
| Malonic acid-di-2-hydroxy-$C_{16/18}$-alkyl ester (A) | 4 |
| Glycerol mono-oleate | 3 |
| Beeswax | 3 |
| Methyl p-hydroxybenzoate | 0.2 |
| Water | 49.8 |

EXAMPLE 2

Cream based on Vaseline ®/paraffin oil/peanut oil

| | Parts by Weight |
|---|---|
| Vaseline ® | 25 |
| Paraffin oil | 20 |
| Peanut oil | 5 |
| Succinic acid-di-2-hydroxy-$C_{16/18}$-alkyl ester (B) | 6 |
| Methyl p-hydroxybenzoate | 0.2 |
| Water | 43.8 |

EXAMPLE 3

Cream based on Vaseline ®/paraffin oil

| | Parts by Weight |
|---|---|
| Vaseline ® | 8 |
| Paraffin oil | 13 |
| Isopropyl myristate | 2 |
| Tartronic acid-di-2-hydroxy-$C_{16/18}$-alkyl ester (E) | 6 |
| Glycerol | 4 |
| Magnesium sulfate . 7 $H_2O$ | 1 |
| Zinc oxide | 2 |
| Methyl p-hydroxybenzoate | 0.2 |
| Water | 63.8 |

EXAMPLE 4

Cream based on Vaseline ®/2-octyldodecanol

| | Parts by Weight |
|---|---|
| Vaseline ® | 25 |
| 2-octyldodecanol | 20 |
| Beeswax | 6 |
| Tartaric acid-di-2-hydroxy-$C_{16/18}$-alkyl ester (M) | 3.5 |
| Aluminium stearate | 1.0 |
| Methyl p-hydroxybenzoate | 0.2 |
| Water | 44.3 |

The other emulsifiers mentioned under A to A' can be used with comparably good results in place of the dicarboxylic acid-di-2-hydroxy-alkyl esters mentioned in the Examples.

The preceding specific examples are illustrative of the practice of the invention. It is to be understood however, that other expedient known to the skilled in the art or disclosed herein, may be employed without departing from the spirit of the invention or the scope of the appended claims.

We claim:

1. Mono- and Dicarboxylic acid esters of 1,2-dihydroxyalkanes of the formulae

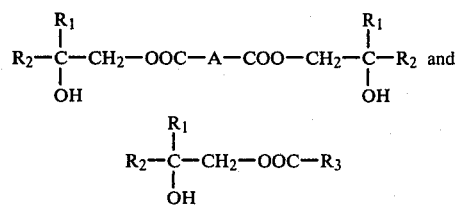

wherein A represents a bivalent radical selected from the group consisting of alkylene having from 1 to 16 carbon atoms, hydroxyalkylene having from 1 to 8 carbon atoms and 1 to 4 hydroxys, alkenylene having from 2 to 18 carbon atoms, alkoxyalkylene having from 2 to 6 carbon atoms, phenylene, alkylphenylene having from 1 to 12 carbon atoms in the alkyl; $R_1$ represents a member selected from the group consisting of hydrogen and alkyl having from 1 to 12 carbon atoms; $R_2$ is alkyl having from 10 to 22 carbon atoms; and $R_3$ represents a member selected from the group consisting of hydroxyalkyl having from 1 to 4 carbon atoms, phenylhydroxyalkyl having from 1 to 4 carbon atoms in the alkyl and haloalkyl having from 1 to 4 carbon atoms.

2. The esters of 1,2-dihydroxyalkane of claim 1 wherein $R_1$ is hydrogen and $R_2$ is alkyl having from 10 to 18 carbon atoms.

3. The esters of 1,2-dihydroxyalkane of claim 1 having the formula

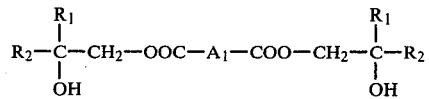

wherein $A_1$ is a member selected from the group consisting of alkylene having from 1 to 4 carbon atoms and alkenylene having from 2 to 4 carbon atoms, $R_1$ is hydrogen and $R_2$ is alkyl having from 10 to 18 carbon atoms.

4. The esters of 1,2-dihydroxyalkane of claim 1 being malonic acid-di-2-hydroxy-$C_{16/18}$-alkyl ester.

5. The esters of 1,2-dihydroxyalkane of claim 1 being succinic acid-di-2-hydroxy-$C_{16/18}$-alkyl ester.

6. The esters of 1,2-dihydroxyalkane of claim 1 being tartronic acid-di-2-hydroxy-$C_{16/18}$-alkyl ester.

7. The esters of 1,2-dihydroxyalkane of claim 1 being tartaric acid-di-2-hydroxy-$C_{16/18}$-alkyl ester.

* * * * *